(12) United States Patent
Olthof

(10) Patent No.: US 10,035,782 B2
(45) Date of Patent: Jul. 31, 2018

(54) RELATING TO ETHYLENE OXIDE RECOVERY

(71) Applicants: SHELL INTERNATIONALE RESEARCH MAATSCHAPPIJ B.V., The Hague (NL); SHELL OIL COMPANY, Houston, TX (US)

(72) Inventor: Timothe Johannes Olthof, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/515,609

(22) PCT Filed: Sep. 29, 2015

(86) PCT No.: PCT/EP2015/072372
§ 371 (c)(1),
(2) Date: Mar. 30, 2017

(87) PCT Pub. No.: WO2016/050741
PCT Pub. Date: Apr. 7, 2016

(65) Prior Publication Data
US 2017/0298035 A1 Oct. 19, 2017

(30) Foreign Application Priority Data
Oct. 1, 2014 (EP) .................................. 14187384

(51) Int. Cl.
*C07D 301/32* (2006.01)
*B01D 3/14* (2006.01)
*B01D 3/00* (2006.01)

(52) U.S. Cl.
CPC ........... *C07D 301/32* (2013.01); *B01D 3/009* (2013.01); *B01D 3/143* (2013.01)

(58) Field of Classification Search
CPC .................................................... C07D 301/32
USPC ........................................................ 549/541
See application file for complete search history.

(56) References Cited

U.S. PATENT DOCUMENTS

| 4,033,617 A | 7/1977 | Cocuzza et al. |
| 4,134,797 A | 1/1979 | Ozero |

FOREIGN PATENT DOCUMENTS

| DE | 3302525 | 7/1984 |
| WO | 2004009572 | 4/2004 |
| WO | 2006120207 | 11/2006 |
| WO | 2010014182 | 2/2010 |

OTHER PUBLICATIONS

Lestak et al.; "Advanced Distillation Savese"; Chemical Engineering, Access Intelligence Association; vol. 7; pp. 72-29; Jul. 1, 1997.
International Search Report dated Feb. 9, 2016; 5 pages.

*Primary Examiner* — Taofiq A Solola

(57) ABSTRACT

A process for recovering an ethylene oxide (EO) enriched product stream from fat absorbent (FA) comprising water, EO, and acetaldehyde. The process comprises passing a feed of FA from a loopgas EO absorber to a multi-stage countercurrent distillation zone, the feed of FA having a concentration of EO in the range of from about 1 to about 15 wt % upon entering the distillation zone; and obtaining from the distillation zone an acetaldehyde enriched stream, a lean absorbent (LA) stream, a vapor stream enriched in light ends, a glycol enriched bottoms stream and an EO enriched product stream. Suitable apparatus is also disclosed.

13 Claims, 3 Drawing Sheets

RELATING TO ETHYLENE OXIDE RECOVERY

PRIORITY CLAIM

The present application is the National Stage (§ 371) of International Application No. PCT/EP2015/072372, filed Sep. 29, 2015, which claims priority from European Patent Application No. 14187384.4, filed Oct. 1, 2014 incorporated herein by reference.

FIELD OF THE INVENTION

This invention relates to the recovery of ethylene oxide (EO). In particular, though not exclusively, this invention relates to energy efficient separation of EO from fat absorbent (FA) comprising water, EO, and acetaldehyde.

BACKGROUND OF THE INVENTION

Ethylene oxide (EO) is a product manufactured worldwide in amounts of several million tonnes per year. The production of EO is described, for example, in Kirk-Othmer Encyclopaedia of Chemical Technology, third edition, Volume 9, 1980, pages 443 to 447.

A conventional EO distillation system is discussed in WO2006/120207, e.g. with reference to FIG. 1 therein. In a conventional system, loopgas from an EO reactor is passed to a loopgas EO absorber where it is absorbed by an aqueous lean absorbent (LA) to form fat absorbent (FA).

The FA then enters a stripper column in which heat is supplied, typically by steam or a reboiler, to produce overhead vapours comprising EO and a bottoms LA stream for recycling. The overhead vapours are condensed and/or reabsorbed to form a stripped, concentrated EO stream.

Where purified EO is required, there follows purification of the stripped EO stream by distillation.

Purification is generally performed in one or more distillation columns. Such columns vary in design but inevitably require reheating of the condensed EO stream to effect distillation. Indeed, in some systems multiple cycles of reheating and condensation occur before EO purification is complete.

Prior art processes for recovering EO, in particular high purity EO comprising at least 99.5 wt % EO, are energy intensive as a result of the heating, condensation and reheating that occurs during stripping and purification. Nevertheless, the traditional approach of stripping followed by purification is engrained in the art.

U.S. Pat. No. 4,134,797A describes a process for recovering ethylene oxide containing low levels of aldehyde impurities using a multi-stage countercurrent distillation zone.

U.S. Pat. No. 4,033,617A describes a process for purifying an aqueous stream containing absorbed ethylene oxide and acetaldehyde, comprising condensations, liquefaction and distillation steps.

It is an object of the invention to provide a more energy efficient solution for recovering EO from FA and/or to solve at least one problem associated with the prior art.

SUMMARY OF THE INVENTION

According to a first aspect of the invention there is provided a process for recovering an ethylene oxide (EO) enriched product stream from fat absorbent (FA) comprising water, glycols, EO and acetaldehyde, the process comprising: passing a feed of FA from a loopgas EO absorber to a multi-stage countercurrent distillation zone, the feed of FA having a concentration of EO in the range of from about 1 to about 15 wt % upon entering the distillation zone; obtaining from the distillation zone an acetaldehyde enriched stream, a lean absorbent (LA) stream, a vapour stream enriched in light ends and an EO enriched product stream, and wherein the FA comprises glycols and the process comprises obtaining from the distillation zone a glycol enriched bottoms stream.

The process involves introducing FA with a relatively low concentration of EO into a countercurrent distillation zone (hereinafter referred to as "the distillation zone"). Pre-concentration steps before the FA enters the distillation zone, such as for example conventional steam stripping of the FA, can be avoided, hence reducing energy requirements.

DETAILED DESCRIPTION OF THE INVENTION

Figure 1:
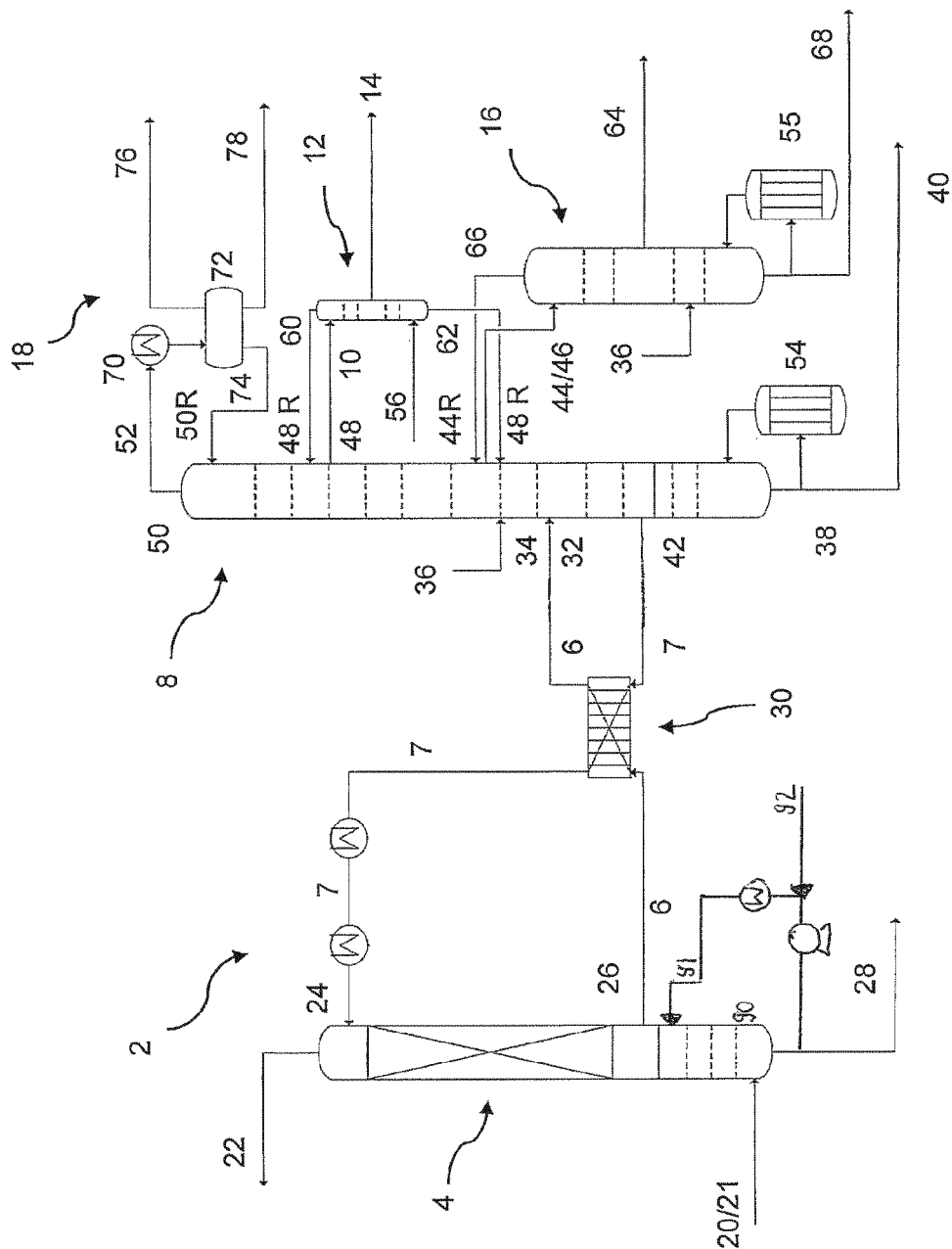
FIG. 1 shows a schematic view of an apparatus for recovering EO in accordance with a first embodiment of the invention.

It has been found, surprisingly and contrary to engrained practice in the art, that pre-concentration by thermic stripping of FA to remove LA and to form a stripped, concentrated FA for subsequent purification can be omitted. Instead, FA can be fed, without being subjected to thermic stripping or other highly energy intensive pre-concentration process to a multi-stage countercurrent distillation zone to obtain an EO enriched product stream, which has a reduced acetaldehyde concentration by virtue of the distinct acetaldehyde enriched stream also obtained from the distillation zone.

The EO enriched product stream may be further processed, for example by stripping as will be described, to provide a purified EO product stream.

In an embodiment, the EO enriched product stream is processed into a high purity EO product stream comprising at least 99.5 wt % EO, preferably at least 99.9 wt % EO. A purified EO product stream can be obtained in this manner with energy savings compared to prior art processes, since the downstream processing of a smaller quantity of EO enriched product stream requires less energy than pre-concentration, e.g. stripping, of FA as a whole.

In an embodiment, the feed of FA entering the distillation zone comprises EO in an amount in the range of from about 1.5 to about 10 wt % EO. Advantageously, the FA entering the distillation zone may comprise EO in an amount in the range of from about 2 to about 8 wt % EO.

The FA is obtained from a loopgas EO absorber. In loopgas EO absorbers, EO contained in loopgas received from an EO reactor is absorbed by lean absorbent (LA) to form the FA. A top gas is recycled to the reactor. The loopgas EO absorber is thus distinct from reabsorbers, such as may be employed further downstream.

EO reactors for producing a)-containing loopgas are known in the art. Typically such reactors oxidise ethylene with air or elemental oxygen over a suitable catalyst, typically a silver-containing catalyst, at elevated temperature (e.g. 100 to 500° C.) and at superatmospheric pressure (e.g. 2 to 25 atmospheres). The particular configuration of the EO reactor is not critical to the understanding of the present invention, which may in principle be used in the recovery of EO from FA obtained from any a)-containing reactor loopgas.

As is known in the art, LA typically comprises water, optional additives, and entrained or accumulated process components. The loopgas EO absorber provides for absorption of EO from the loopgas into the LA to form FA in known fashion. Typical arrangements for facilitating absorption include countercurrent contact between the LA and loopgas. The particular configuration of the absorber is not critical to the understanding of the present invention, which may in principle be used in the recovery of EO from FA produced in any EO absorber.

The composition of the FA feed exiting the absorber may vary, for example depending on the precise nature and operation of the EO reactor and the loopgas EO absorber. Typically the FA exiting the absorber will comprise, in addition to EO and water, by-products of ethylene oxidation. In addition to acetaldehyde, such by-products may include, for example, formaldehyde, carbon dioxide and organic acids. Glycols are also formed in the FA.

In the process of the invention, the FA feed is passed from the loopgas EO absorber to the distillation zone. The FA feed may flow under gravity and/or be driven by a pressure differential as is known in the art.

In an embodiment, the FA is passed to the distillation zone substantially in the form in which the FA exits the absorber, i.e. without subjecting the FA to processing steps that substantially alter EO concentration. Alternatively, in principle, the FA could be subjected to one or more processing steps between the absorber and the distillation zone, provided that the concentration of EO on entering the distillation zone remains as defined hereinabove. However, it is preferred to pass the FA to the distillation zone directly.

In an embodiment, the process comprises heating the FA between the absorber and the distillation zone. Advantageously, the FA may be heated to a temperature in the range of from about 25 to about 140° C. on entering the distillation zone, for example a temperature in the range of from about 100 to about 110° C. Advantageously, the process may comprise heat-exchanging the LA stream with the FA feed passed to the distillation zone, and recycling at least part of the LA stream to the loopgas EO absorber.

In the distillation zone, the FA feed is separated into at least the acetaldehyde enriched stream, the lean absorbent (LA) stream, the vapour stream enriched in light ends and the EO enriched product stream. Depending on upstream process conditions also a formaldehyde enriched stream is recovered.

A glycol enriched bottoms stream (also referred to as "glycol bleed") is also obtained from a bottoms section of the FA in the distillation zone. The glycol bleed typically comprises, in addition to one or more glycols and other impurities, considerable (balancing) amounts of water. In an embodiment, the glycol bleed comprises in the range of from 10 to 90 wt %, for example in the range of from 40 to 80 wt %, monoethylene glycol (MEG) and/or diethylene glycol (DEG) and/or triethylene glycol (TEG) as well as heavier glycols and other high boiling components.

The acetaldehyde enriched stream may be a side-stream obtained from a side draw of the distillation zone. The acetaldehyde enriched stream typically comprises, in addition to acetaldehyde, significant amounts of EO. In an embodiment, the acetaldehyde enriched stream comprises in the range of from 500 to 30,000 ppmw, for example in the range of from 2,000 to 20,000 ppmw acetaldehyde. In an embodiment, the acetaldehyde enriched stream comprises in the range of from 80 to 99 wt % EO, for example in the range of from 90 to 98 wt % EO.

The acetaldehyde enriched stream may be further concentrated. In an embodiment the process comprises passing the acetaldehyde enriched stream to a concentrator column and obtaining a concentrated acetaldehyde bleed and one or more other streams, in particular comprising EO, which other streams may optionally be recycled to the distillation zone. Suitably the concentrated acetaldehyde bleed may be obtained as a side-bleed from the concentrator column, and an overhead stream of the concentrator may be recycled to the distillation zone. In an embodiment, the concentrated acetaldehyde bleed may have an acetaldehyde concentration of at least 4000 ppmw, preferably at least 30,000 ppmw.

The LA stream may be a side-stream, obtained from a side draw of the distillation zone. In an embodiment, the LA stream comprises predominantly water, and an EO content of less than 500 ppmw, preferably less than 100 ppmw, more preferably less than 10 ppmw. Glycols (e.g. as defined hereinabove) and other trace components may also be present in the LA stream, but are preferably present in an amount of less than 15 wt %, more preferably less than 10 wt %.

In an embodiment, the process comprises recycling at least part of the LA stream to the loopgas absorber. Advantageously, the process may comprise cooling the LA stream before it enters the loopgas absorber, e.g. to a temperature in the range of from 10 to 40° C. As aforesaid, the process may comprise heat-exchanging the LA stream with the FA feed passed to the distillation zone prior to recycling to the loopgas absorber.

The vapour stream enriched in light ends may be obtained from the distillation zone as an overhead vapour stream after (partial) condensation of the EO vapours to provide a reflux for said distillation zone. The vapour stream will contain balancing amounts of the incondensables that were dissolved in the FA and will not be sent with any of the other product streams, as well as some EO vapour.

In an embodiment, this overhead vapour stream enriched in light ends may advantageously be sent to a reabsorber column to absorb and recover the EO vapour from said stream. The overhead stream of said reabsorber column may advantageously be sent to a compressor to recover the light ends and send them to the EO reactor gas loop.

The formaldehyde enriched stream may be recovered, if advantageous, as a bleed stream from the liquids collected after (partial) condensation of the overhead vapours. The formaldehyde enriched stream typically comprises, in addition to formaldehyde, significant amounts of EO. In an embodiment, the formaldehyde enriched stream comprises in the range of from 10 to 1,500 ppmw, for example in the range of from 50 to 150 ppmw formaldehyde.

The EO enriched product stream may advantageously be obtained from the distillation zone as a side-stream. Additionally or alternatively, an EO enriched product stream may be obtained as an overhead stream comprising overhead vapours from the distillation zone, which may be condensed and optionally reabsorbed for further processing.

In general, overhead vapours from the distillation zone may be at least partly refluxed to the distillation zone, for example following condensation. Conveniently, a bleed, for example for formaldehyde, may be drawn from the overhead vapours.

In an embodiment, the EO enriched product stream comprises at least 99.5 wt %, preferably at least 99.9 wt % EO. Concentrations of aldehyde and water in the EO enriched product stream may advantageously be below thresholds set in one or more specifications for high purity EO. In an embodiment, the EO enriched product stream comprises (if any): in the range of from 0 to 300 ppm, preferably in the range of from 0 to 100 ppmw water; and/or in the range of from 0 to 100 ppmw, preferably in the range of from 0 to 20 ppmw aldehyde (as acetaldehyde).

The EO enriched product stream may still comprise a substantial concentration of light ends (incondensables such as carbon dioxide), which may be undesirable.

In an embodiment, the EO enriched product stream exiting the distillation zone comprises in the range of from 100 to 500 ppmw light ends.

As aforesaid, the process may comprise stripping or otherwise further purifying the EO enriched product stream to provide a purified EO product stream, which may advantageously meet a high purity EO specification and/or comprise at least 99.5 wt %, preferably at least 99.9 wt % EO. Such stripping may advantageously reduce the concentration by weight of light ends, e.g. by at least 50%, preferably at least 70%.

Stripping or purification of the EO enriched product stream may be performed in any suitable manner.

In an embodiment, the stripping is performed in a dedicated light ends stripper. Such stripping of the EO enriched product stream may yield a high purity EO product stream and one or more other streams for recycling to the distillation zone.

In an embodiment the stripping comprises countercurrent contact between the EO enriched product stream and a gas (for example open steam, nitrogen or methane) and/or water. In an embodiment, the EO enriched product stream may thus advantageously be purified without further distillation.

Alternatively, in an embodiment, the stripping comprises distillation of the EO enriched product stream by the introduction of heat, e.g. through a steam feed and/or a reboiler. In such arrangements a purified EO product stream may be obtained as a bottoms or side-stream product.

As a further alternative, the stripping may be performed in an integrated fashion. In an embodiment, the process comprises stripping light ends from the EO enriched product stream within a stripping zone defined within a divided wall column housing the countercurrent distillation zone.

To maintain a water balance in the distillation zone, and to aid separation of EO, the process may comprise feeding water into the distillation zone via a separate water feed. Advantageously, water may be fed into the distillation zone above the FA. In an embodiment, water is fed into the distillation zone below an outlet for the acetaldehyde enriched stream, and/or within one or two equilibrium trays of such an acetaldehyde outlet.

In one advantageous embodiment, the process is provided for recovering an ethylene oxide (EO) enriched product stream from fat absorbent (FA) comprising water, EO, acetaldehyde, formaldehyde and incondensables and comprises: passing a feed of FA from a loopgas EO absorber to a multi-stage countercurrent distillation zone, the feed of FA having a concentration of EO in the range of from about 1 to about 15 wt % upon entering the distillation zone; optionally feeding water into the distillation zone; and obtaining from the distillation zone an acetaldehyde enriched stream, a lean absorbent (LA) stream, an EO side-stream constituting an EO enriched product stream, a glycol enriched bottoms stream and an overhead stream comprising incondensables, the streams and feeds optionally being, or being further processed, as hereinabove described.

In another advantageous embodiment, the process is provided for recovering an ethylene oxide (EO) enriched product stream from fat absorbent (FA) comprising water, EO, acetaldehyde, formaldehyde and incondensables and comprises: passing a feed of FA from a loopgas EO absorber to a multi-stage countercurrent distillation zone, the feed of FA having a concentration of EO in the range of from about 1 to about 15 wt % upon entering the distillation zone; optionally feeding water into the distillation zone; and obtaining from the distillation zone an acetaldehyde enriched stream, a lean absorbent (LA) stream, an EO overhead stream constituting an EO enriched product stream, and a glycol enriched bottoms stream, the streams and feeds optionally being, or being further processed, as hereinabove described.

From a second aspect, the invention resides in apparatus for recovering an EO enriched product stream from fat absorbent (FA) comprising water, acetaldehyde, glycols, and ethylene oxide (EO) in a concentration in the range of from about 1 to about 15 wt %, the apparatus comprising a multi-stage countercurrent distillation column comprising: a FA inlet, an aldehyde outlet for an acetaldehyde enriched stream, a lean absorbent (LA) outlet for a LA stream, and an EO outlet for an EO enriched product stream.

The apparatus may be adapted to perform a process in accordance with the first aspect of the invention, e.g. as described anywhere hereinabove. Suitable components of the apparatus may be configured accordingly by those skilled in the art.

The apparatus is arranged for recovering an EO enriched product stream from fat absorbent (FA) comprising water, EO, acetaldehyde and glycols, with the multi-stage countercurrent distillation column comprising: a FA inlet, a glycol bottoms outlet, a LA side draw constituting the LA outlet, an acetaldehyde side draw constituting the acetaldehyde outlet, and the EO outlet. The EO outlet may suitably be a side-draw or an overhead outlet.

In an embodiment the apparatus comprises a loopgas EO absorber, e.g. as hereinabove described, and a conduit for transporting FA from the loopgas EO absorber to the distillation column. In an embodiment, the conduit comprises one or more heat exchangers. Advantageously, the heat exchanger(s) may be in fluid communication with the LA outlet of the distillation column to effect heat exchange between FA flowing to the FA inlet of the distillation column and LA flowing from the LA outlet to the loopgas EO absorber via a recycling conduit. Optionally the apparatus may comprise one or more further coolers for reducing the temperature of LA in the LA recycling conduit.

In an embodiment, the conduit is arranged to transport the FA from the loopgas EO absorber to the distillation column without substantially increasing the EO concentration of the FA feed, for example without increasing the EO concentration by more than 5 wt % based on the total feed.

The multi-stage countercurrent distillation column (hereinafter referred to as "the distillation column") defines a multi-stage countercurrent distillation zone ("the distillation zone") in which the FA feed can be separated into at least the acetaldehyde enriched stream, the lean absorbent (LA) stream, and the EO enriched product stream, and a glycol enriched bottoms stream. The distillation column may be arranged such that one or more of said streams is obtained as described anywhere herein.

The distillation column may be arranged and configured in any manner consistent with obtaining the desired streams.

The distillation column comprises a plurality of distillation regions each having means for providing countercurrent contact between downflowing liquid and upwardly flowing vapour. In an embodiment, the distillation column comprises a base fractionation region of at least five, preferably at least ten, theoretical vapour-liquid contacting stages below the FA inlet and, in ascending order above the FA inlet, the following further fractionation regions:

- a first fractionation region of at least fifteen, preferably at least thirty, theoretical vapour-liquid contacting stages, the acetaldehyde outlet being arranged to withdraw from the column at least a portion of the downflow from the first fractionation region; and
- a second fractionation region of at least one, preferably between one and five, theoretical vapour-liquid contacting stages, the EO outlet being arranged to withdraw from the column at least a portion of the downflow from the second fractionation region.

In an embodiment, the distillation column comprises a reboiler for drawing liquid from a bottoms or base region of the column, heating the liquid and recycling heated liquid to the column. A glycol bottoms outlet is arranged to allow at least part of the liquid from the bottoms region to be removed as a bleed.

In an embodiment, the apparatus comprises a concentrator in fluid communication with the acetaldehyde outlet. The concentrator may be arranged to concentrate an acetaldehyde enriched stream exiting the distillation column via the acetaldehyde outlet into a more concentrated acetaldehyde bleed having a higher concentration of acetaldehyde, and to feed a return stream comprising EO to the distillation column.

In an embodiment, the concentrator comprises a concentrator column comprising: an inlet in fluid communication with the acetaldehyde outlet of the distillation column; a concentrator side-draw or bottoms outlet for obtaining a concentrated acetaldehyde bleed from the concentrator; and an overhead and/or bottoms outlet for one or more return feeds or bleeds. The apparatus may comprise conduits for recycling fluid from the overhead and/or bottoms outlet to the distillation column and/or concentrator column.

The apparatus may define a light ends stripping zone arranged to strip light ends from EO enriched product stream exiting the distillation zone via the EO outlet. The light ends stripping zone may be arranged to lower or eliminate the concentration of one or more residual light impurities, in particular carbon dioxide and other light ends and/or formaldehyde, in the EO enriched product stream to form a purified EO product.

The light ends stripping zone may be defined by a stripper in fluid communication with the EO outlet, for stripping EO enriched product stream received from the EO outlet of the distillation column. Additionally or alternatively, the distillation column may be a divided wall column housing the light ends stripping zone.

The light ends stripping zone may comprise liquid/vapour contacting trays or other mass transfer internals.

Where the apparatus comprises a dedicated stripper, the stripper may comprise a countercurrent column with an inlet for a stripping gas (such as for example nitrogen, methane or steam) that is allowed in the final product. Additionally, or alternatively, the stripper may comprise a reboiler or steam inlet for supplying heat to effect stripping. In an embodiment, the stripper comprises an inlet for water or another component with a higher boiling point than EO to prevent the occurrence of pure EO in the reboiler.

Advantageously, the distillation column may comprise an overhead reflux system as is known in the art.

In an embodiment, the distillation column comprises a water inlet, to allow additional water to be introduced into the distillation column to meet a desired water balance and aid EO separation, in particular from formaldehyde.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

DETAILED DESCRIPTION OF THE DRAWINGS

Figure 2:
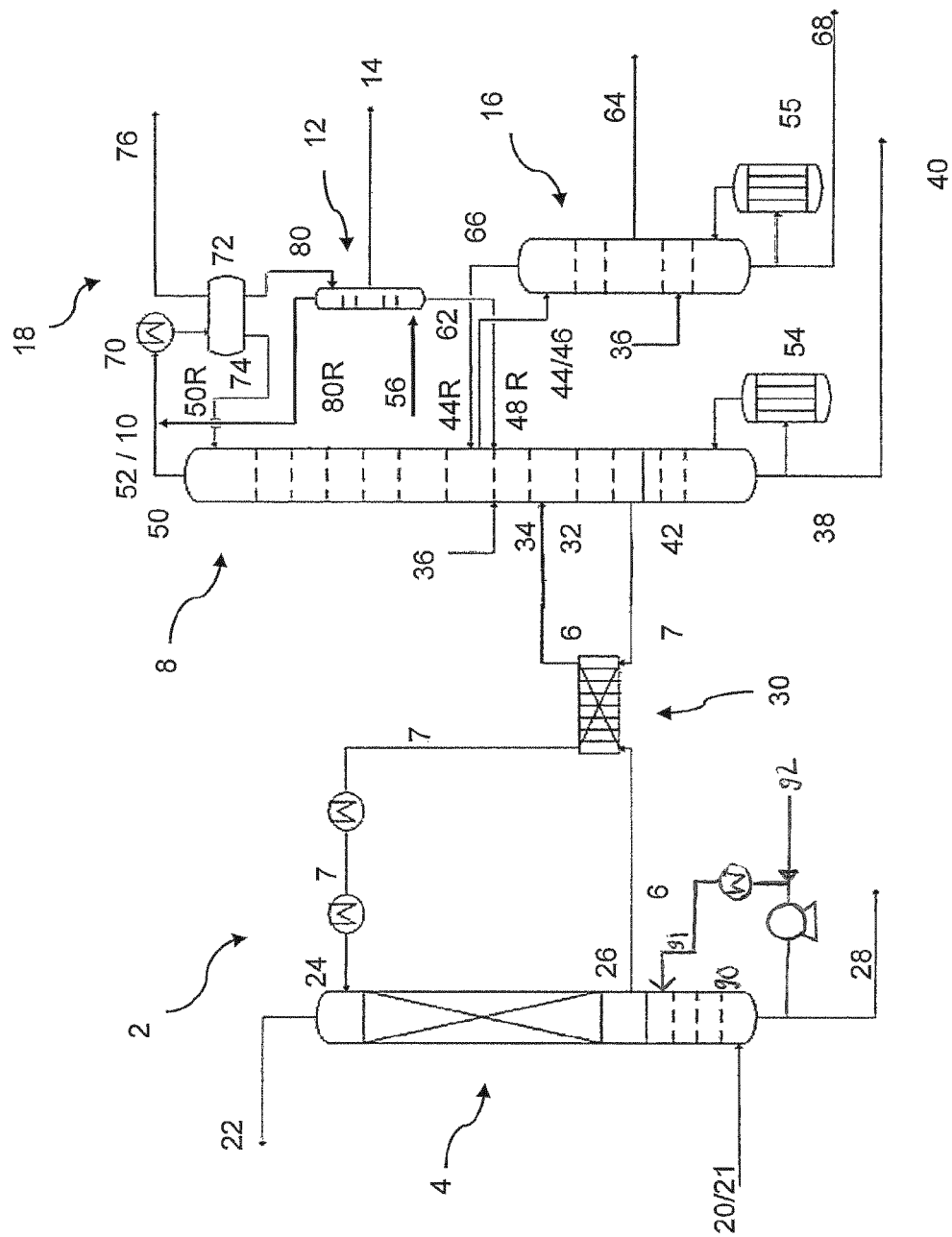
FIG. 2 shows a schematic view of an apparatus for recovering EO in accordance with a second embodiment of the invention.
Figure 3:
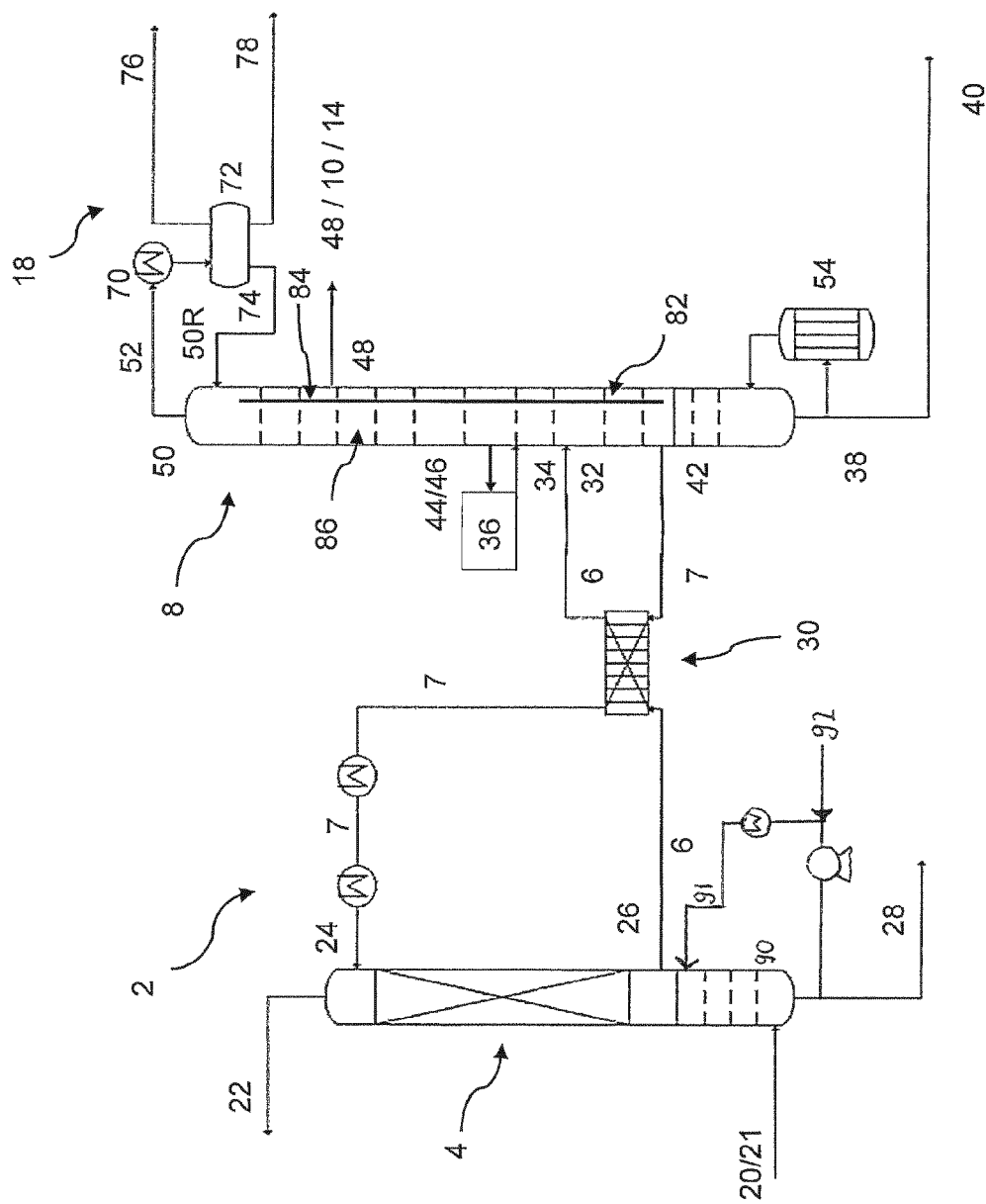
FIG. 3 shows a schematic view of an apparatus for recovering EO in accordance with a third embodiment of the invention.

Embodiments of the present invention will now be further described, by way of non-limiting examples, with reference to the accompanying FIGS. 1 to 3.

With reference to FIG. 1, in a first embodiment of the invention, an apparatus 2 for recovering ethylene oxide (EO) broadly comprises an EO absorber 4 for producing a feed of fat absorbent (FA) 6, a multi-stage countercurrent distillation column 8 for recovering an EO enriched product stream 10 from the FA, a light ends (LE) stripper 12 for stripping the EO enriched stream 10 to produce an EO product 14, an acetaldehyde concentrator 16, and an overhead/reflux system 18.

The EO absorber 4 is of conventional design, comprising a loopgas inlet 21 for receiving EO-containing loopgas 20 from an EO reactor (not shown). The EO absorber 4 also comprises a topgas outlet 22, an inlet 24 for receiving water-based lean absorbent (LA) 7 and an outlet 26 for FA 6. The EO absorber 4 comprises beds of structured packing or trays (not shown). In use, the EO-containing reactor loopgas 20 passes through quench section 90 where it is scrubbed with a cooled recirculating, slightly alkaline aqueous quench stream 91. Quench make up solution 92 may optionally be added to the recirculating aqueous solution 91 in the quench section. LA is then contacted with the resultant EO-containing loopgas over the packing to absorb EO from the loopgas and form FA 6, which leaves the absorber via the FA outlet 26. Loopgas 20 leaving the overhead 22 outlet as topgas has a depleted EO-content and is recycled to the EO reactor. A quench bleed 28 is also drawn from the EO absorber 4 and processed in conventional fashion.

The FA outlet 26 of the EO absorber is connected to a heat exchanger 30, where the FA 6 is heated. A further conduit passes the heated FA 6 into the distillation column 8 via an FA inlet 32 thereof.

The distillation column 8 comprises, in addition to the FA inlet 32, an inlet 34 for a water feed 36. In terms of outlets, the column 8 comprises a bottoms outlet 38 for a glycol bleed 40, a side draw 42 for LA 7, a side draw 44 for an acetaldehyde enriched stream 46, a side draw 48 for the EO enriched stream 10, and an overhead outlet 50 for overhead vapours 52. The column 8 also comprises a return 44R from the acetaldehyde concentrator 16, two returns 48R from the LE stripper 12, and a return 50R from the reflux system 18. Heat is supplied to the column by a reboiler 54.

The inlets, outlets and general structure of the distillation column 8 are arranged to enable distillation of the FA 6 to provide the EO enriched stream 10, which typically comprises less than 25 ppmw formaldehyde and acetaldehyde but still includes significant amounts of light components (incondensables such as carbon dioxide).

In an exemplary embodiment, the outlet 48 for the EO stream 10 is placed in the range of from 50 to 75 equilibrium trays above the FA feed 32, and a small number of equilibrium trays below the overhead outlet 50 of the column. The outlet 44 for the acetaldehyde enriched stream 46 is placed a small number of equilibrium trays above the FA feed 32, as is the inlet 34 for water feed 36. The outlet 42 for LA 7 is placed in the range of from 10 to 17 equilibrium trays under the FA feed.

To eliminate light components, the EO enriched stream 10 is fed to the LE stripper 12 in which it is contacted with vapour generated by open steam 56 in the bottom of the stripper 12. A final product stream 14 is obtained a small number equilibrium trays under a top return 60 and in the range of from 12 to 25 equilibrium trays above the open steam feed 56. A water bleed 62 (with traces EO) is fed back to the EO purification column 8 at approximately the same height as the water feed 36.

The acetaldehyde enriched stream 46 is fed to the concentrator 16. The concentrator 16 further concentrates the acetaldehyde enriched stream 46 so as to maximise the recovery of high purity EO from the FA 6 and minimise the size of the acetaldehyde enriched bleed stream 46. The concentrator 16 is heated by a reboiler 55 and comprises in the range of from 20 to 40 equilibrium trays. A concentrated acetaldehyde enriched bleed stream 64 is retrieved four equilibrium trays from the bottom of the concentrator 16 and removed from the apparatus 2, e.g. to a glycols section, whereas the vapour generated in the concentrator overhead 66 is sent back to the EO purification column 8. To prevent the accumulation of a high concentration of glycols in the bottom of the concentrator 16, condensate 36 is added in the bottom of the concentrator 16 and a water/glycol bleed 68 is retrieved from the sump of the concentrator 16, e.g. to be sent to a glycol section.

The LA outlet 42 is connected to the heat exchanger 30, where an LA stream 7 exiting the distillation column 8 is heat exchanged with FA 6 flowing from the EO absorber 4 to the FA inlet 32 of the distillation column 8. Part of the LA 7 is fed to the bottom trays of the column 8 (either via an external line or a partial draw-off tray, not shown) where glycols built up in the absorbent loop are concentrated and bled in a glycol bleed 40. The remaining LA is returned to the EO absorber 4.

The overhead outlet 50 is connected to a condenser 70, from where condensed liquid flows to a separator 72. The condensed liquid is returned as a liquid reflux 74 to the distillation column 8, whereas the incondensables 76 (in vapour phase, containing some EO) are sent to a residual absorber (not shown). Optionally, formaldehyde may be removed from the system by a formaldehyde bleed 78 from the condenser 72.

The apparatus 2 may be operated to provide an EO product 14 comprising at least 99.5 wt % EO from loopgas. In particular, FA 6 having an EO content of about 4 wt % may be obtained from the absorber 4, heated to a temperature in the range of from about 40 to about 110° C. in the heat exchanger 30 and introduced into the distillation column 8. The feeds and bleeds in the column may be adjusted to provide the desired EO product. In one example, the concentrated acetaldehyde bleed 64 is set at a mass flow in the range of from 2 to 7% of the HPEO product 14 flow, the water feed 36 is set to a mass flow of from 15 to 30% of the HPEO product 14 flow, the reflux is subcooled to 29° C. to keep the vapour phase, containing EO, out of the flammable range in the overhead separator vessel 72, the reflux flow is set to in the range of from 3 to 5 times the HPEO product 14 flow, and in the bottoms region a glycol concentration of from 10 to 30 wt % is used.

Alternative modes of operation and configurations will be apparent to those skilled in the art in light of the foregoing description.

For example, the distillation column 8 and/or concentrator 16 could be re-designed to work with open steam instead of the reboiler 54 and 55. Similarly, the LE stripper 12 could be re-designed to comprise a reboiler or to have only an overhead return, e.g. with nitrogen gas being used for stripping.

Indeed, even more substantial structural modifications could be made to the design of the apparatus without departing from the invention.

In one alternative embodiment, the EO enriched stream is obtained from the overhead vapours 52, following condensation. Referring now to FIG. 2, in which like reference numerals are used for like parts, the overhead vapours are condensed and separated into a reflux 74, an EO rich condensate 80 fed to the light ends stripper 12. The EO product 14 is obtained as a side draw from the light ends stripper 12 and the overhead vapours 80R of the light ends stripper 12 are returned to the condenser 70. A bottoms return 48R returns a water rich stream from the light ends stripper 12 to the distillation column 8.

In another alternative embodiment, stripping of the EO enriched stream is achieved within the distillation column 8 by creating a stripping zone 82 with an internal dividing wall 84, thus eliminating the need for a separate stripper column 12. Referring now to FIG. 3, in which like reference numerals are used for like parts, the column 8 is formed as a dividing-wall column, with an a side draw 48 from the stripping zone 82 providing an EO enriched stream 10 which is a purified EO product 14. An acetaldehyde enriched stream 46 is drawn from a side draw 44 from a remaining distillation zone 86 of the column and may optionally be passed to a concentrator (as described with reference to FIG. 1 or 2) with a return (not shown) fed to the remaining distillation zone 86.

That which is claimed is:

1. A process for recovering an ethylene oxide (EO) enriched product stream from fat absorbent (FA) comprising water, EO, and acetaldehyde, the process comprising:

passing a feed of FA from a loopgas EO absorber to a multi-stage countercurrent distillation zone, the feed of FA having a concentration of EO in the range of from 1 to 15 wt % upon entering the distillation zone; and obtaining from the distillation zone an acetaldehyde enriched stream, a lean absorbent (LA) stream, a vapour stream enriched in light ends and an EO enriched product stream, and wherein the FA comprises glycols and the process comprises obtaining from the distillation zone a glycol enriched bottoms stream.

2. The process of claim 1 comprising stripping light ends from the EO enriched product stream to provide a purified EO product stream.

3. The process of claim 1, wherein the feed of FA entering the distillation zone comprises in the range of from 1.5 to 10 wt % EO, preferably in the range of from 2 to 8 wt % EO.

4. The process of claim 1, comprising heat-exchanging the LA stream with the FA feed passed to the distillation zone, and recycling at least part of the LA stream to the loopgas EO absorber.

5. The process of claim 1, comprising passing the acetaldehyde enriched stream to a concentrator to obtain a concentrated acetaldehyde bleed and one or more other streams recycled to the distillation zone.

6. The process of claim 1, wherein the EO enriched product stream is obtained from the distillation zone as a side-stream or as an overhead stream.

7. The process of claim 1, comprising stripping light ends from the EO enriched product stream by countercurrent contact between the EO enriched product stream and a gas.

8. Apparatus for recovering an EO enriched product stream from fat absorbent (FA) comprising water, acetaldehyde, glycols, and ethylene oxide (EO) in a concentration in the range of from 1 to 15 wt %, the apparatus comprising a multi-stage countercurrent distillation column comprising: a FA inlet, an aldehyde outlet for an acetaldehyde enriched stream, a lean absorbent (LA) outlet for a LA stream, and an EO outlet for an EO enriched product stream, wherein the multi-stage countercurrent distillation column comprises:
a FA inlet,
a glycol bottoms outlet,
a LA side draw constituting the LA outlet,
an acetaldehyde side draw constituting the acetaldehyde outlet, and
the EO outlet, and wherein the distillation column comprises a base fractionation region of at least five, theoretical vapour-liquid contacting stages below the FA inlet and, in ascending order above the FA inlet, the following further fractionation regions:
a first fractionation region of at least fifteen, theoretical vapour-liquid contacting stages, the acetaldehyde outlet being arranged to withdraw from the column at least a portion of the downflow from the first fractionation region; and
a second fractionation region of at least one, theoretical vapour-liquid contacting stages, the EO outlet being arranged to withdraw from the column at least a portion of the downflow from the second fractionation region.

9. The apparatus of claim 8, wherein the EO outlet is a side-draw or an overhead outlet.

10. The apparatus of claim 8 further comprising a loopgas EO absorber and a conduit for transporting FA from the loopgas EO absorber to the distillation column, the conduit comprising one or more heat exchangers in fluid communication with the LA outlet to effect heat exchange between FA flowing to the inlet of the distillation column and LA flowing from the LA outlet.

11. The apparatus of claim 8 comprising a concentrator in fluid communication with the acetaldehyde outlet, the concentrator being arranged to concentrate acetaldehyde enriched stream exiting the distillation column via the acetaldehyde outlet into a more concentrated acetaldehyde bleed having a higher concentration of acetaldehyde, and to feed a return stream comprising EO to the distillation column.

12. The apparatus of claim 8 defining a light ends stripping zone arranged to strip light ends from EO enriched product stream exiting the distillation zone via the EO outlet.

13. The apparatus of claim 8 wherein the distillation column as well as the concentrator and/or the light ends stripping zone are integrated into a single column shell.

* * * * *